(12) United States Patent
Bajor et al.

(10) Patent No.: US 6,355,686 B1
(45) Date of Patent: Mar. 12, 2002

(54) COSMETIC COMPOSITIONS CONTAINING SUBSTITUTED AMINE DERIVATIVES

(75) Inventors: John Steven Bajor, Ramsey; David Joseph Pocalyko, Wayne, both of NJ (US)

(73) Assignee: Unilever Home and Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/873,000

(22) Filed: Jun. 1, 2001

Related U.S. Application Data

(60) Provisional application No. 60/215,519, filed on Jun. 30, 2000.

(51) Int. Cl.⁷ .......................... A61K 31/135; A61K 6/00
(52) U.S. Cl. ....................................... 514/646; 424/401
(58) Field of Search ........................... 424/401; 514/646

(56) References Cited

U.S. PATENT DOCUMENTS 3,853,926 A * 12/1974 Tyner ........................ 552/646
3,989,719 A * 11/1976 Mueller ...................... 540/547
5,690,948 A * 11/1997 McCook et al. ............ 424/401

OTHER PUBLICATIONS

Co-pending Application: Bajor et al., S/N: 60/215,648, Filed: Jun. 30, 2000.

Co-pending Application: Bajor et al., S/N: 60/215,535, Filed: Jun. 30, 2000.

Co-pending Application: Bajor et al., S/N: 60/215,520, Filed: Jun. 30, 2000.

* cited by examiner

*Primary Examiner*—Michael G. Hartley
*Assistant Examiner*—Michael Willis
(74) *Attorney, Agent, or Firm*—Ellen Plotkin

(57) ABSTRACT

Cosmetic methods and compositions containing selected substituted secondary amine aromatic compounds. The inventive compositions provide control of sebum secretion from sebocytes, improved oil control and improved feel, and prevent shine and stickiness.

4 Claims, No Drawings

COSMETIC COMPOSITIONS CONTAINING SUBSTITUTED AMINE DERIVATIVES

This application claims benefit to provisional application 60/215,519, filed Jun. 30, 2000.

FIELD OF THE INVENTION

Cosmetic methods and compositions containing secondary amine aromatic derivatives.

BACKGROUND OF THE INVENTION

A frequent, undesirable skin condition is "oily skin," the condition which results from the excessive amount of sebum on the skin. Sebum is skin oil which is produced by sebocytes (cells of the sebaceous glands in the skin) and is then secreted to the skin surface. Oily skin is associated with a shiny, undesirable appearance and a disagreeable tactile sensation. Oily skin affects various age groups. Cosmetic products which provide sebum control are highly desirable.

SUMMARY OF THE INVENTION

The present invention includes, in its first aspect, a cosmetic composition comprising:

(i) from about 0.001% to about 50% of a substituted secondary amine aromatic derivative

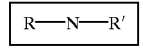

selected from the group consisting of compounds A, B, C, D and E as follows:

-continued

| Compound | R | R' |
|---|---|---|
| D | 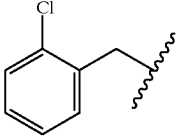 | 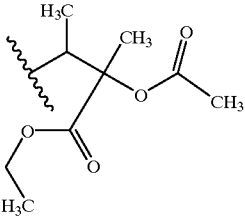 |
| E | 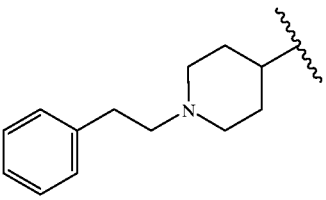 | 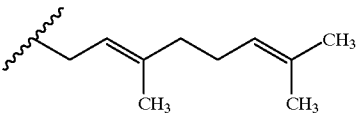 | and (ii) a cosmetically acceptable vehicle.

The present invention also includes a method of controlling or preventing an oily skin condition, especially in the facial area, by applying to the skin the inventive composition.

The invention also includes a cosmetic method of reducing, preventing or controlling sebum secretion from sebocytes by applying to the skin the inventive composition.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

Cosmetic compositions within the scope of the invention are generally personal care compositions including but not limited to skin care compositions (leave-on or rinse-off), hair care compositions (shampoos and conditioners and hair tonics), dentifrices (toothpastes and mouthwashes), and lipsticks and color cosmetics. Inventive compositions may be in the form of lotions, creams, gels, soap bars, shower gels, toners, and face masks.

The preferred compositions are skin care compositions, in order to deliver anti-sebum benefit to the skin.

The term "skin" as used herein includes the skin on the face, neck, chest, back, arms, hands, legs and scalp. The inventive methods and compositions include the substituted secondary amine aromatic derivative

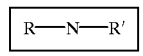

selected from the group consisting of compounds A, B, C, D and E as follows:

| Compound | R | R' |
|---|---|---|
| A | 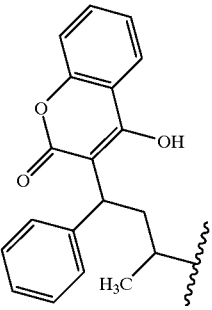 | 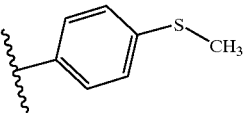 |

-continued

| Compound | R | R' |
|---|---|---|
| B | [structure: benzyl-S-CH2-CH(CH2OH)-] | [structure: -CH(CH2CH2-piperidine)-phenyl-O-CH2CH2CH2-CH3] |
| C | [structure: 2,5-dimethoxyphenyl-CH(CH3)-] | [structure: geranyl group -CH2-CH=C(CH3)-CH2-CH2-CH=C(CH3)-CH3] |
| D | [structure: 2-chlorobenzyl-] | [structure: -C(CH(CH3)2)(C(=O)OCH2CH3)(OC(=O)CH3)] |
| E | [structure: 1-(2-phenylethyl)piperidin-4-yl-] | [structure: geranyl group -CH2-CH=C(CH3)-CH2-CH2-CH=C(CH3)-CH3] |

The substituted secondary amine aromatic derivatives are employed in the present invention in an amount of from 0.0001% to 50%, preferably from 0.0001% to 10%, most preferably from 0.0001% to 5%.

The substituted secondary amine aromatic derivatives can be obtained from New Chemical Entities, Inc. (Bothell, Wash.).

The compositions according to the invention comprise a cosmetically acceptable vehicle to act as a diluant, dispersant or carrier for the substituted secondary aromatic amine in the composition, so as to facilitate its distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 40 to 90%, optimally between 60 and 90% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, poly propylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners Will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients and sunscreens.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

A preferred additional anti-sebum agent is a retinoid. It has been found that compounds B, C, D, E had improved sebum suppressive activity in the presence of a retinoid. Compounds D and E had sebum suppressive active only in the presence of a retinoid. Retinoids (e.g. retinol/retinyl ester/retinal/retinoic acid) are present in the epidermis, so compounds D and E will have the sebum suppressive activity when applied to the skin. The preferred compositions, however, include a retinoid as an additional ingredient.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are C1–C30 esters of retinol, preferably C2–C20 esters, and most preferably C2, C3, and C16 esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

The preferred ester for use in the present invention is selected from retinyl palmitate, retinyl acetate and retinyl propionate, because these are the most commercially available and therefore the cheapest. Retinyl ester is also preferred due to its efficacy.

The retinoid is employed in the inventive composition in an amount of from about 0.001% to about 10%, preferably in an amount of from about 0.01% to about 1%, most preferably in an amount of from about 0.01% to about 0.5%.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

The composition according to the invention is intended primarily as a product for topical application to human skin, especially as an agent for controlling or preventing excessive sebum secretion.

In use, a quantity of the composition, for example from 1 to 100 ml, is applied to exposed areas of the skin, from a suitable container or applicator and, if necessary, it is then spread over and/or rubbed into the skin using the hand or fingers or a suitable device. Product Form and Packaging:

The cosmetic composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

EXAMPLE 1

Compounds A through E were tested for their potential to suppress sebum expression, alone or in the presence of a retinoid.

Secondary cultures of human sebocytes obtained from an adult male were grown in 48-well tissue culture plates (Costar Corp.; Cambridge, Mass.) or 96-well tissue culture plates (Packard Co.; Meriden, Conn.) until confluent. Sebocyte growth medium consisted of Clonetics Keratinocyte Basal Medium (KBM) supplemented with 14 $\mu$g/ml bovine pituitary extract, 0.4 $\mu$g/ml hydrocortisone, 5 $\mu$g/ml insulin, 10 ng/ml epidermal growth factor, 1.2×10−10 M cholera toxin, 100 units/ml penicillin, and 100 $\mu$g/ml streptomycin. All cultures were incubated at 37° C. in the presence of 7.5% $CO_2$. Medium was changed three times per week.

On the day of experimentation, the growth medium was removed and the sebocytes washed three times with sterile Dulbecco's Modified Eagle Medium (DMEM; phenol red free). Fresh DMEM was added to each sample (duplicates, triplicates, or quadruplicates depending on the experiment) with 5 microliter of test agent solubilized in ethanol either alone or in the presence of one or 10 micromolar of retinol. Controls consisted of addition of ethanol alone, retinol alone, or phenol red, which has estrogen-like activity and is included as a positive control.

Each plate was returned to the incubator for 20 hours followed by the addition of 14C-acetate buffer (5 mM final concentration, 56 mCi/mmol specific activity). Sebocytes were returned to the incubator for four hours after which each culture was rinsed three times with phosphate buffered saline to remove unbound label. Radioactive label remaining in the sebocytes was harvested and counted using a Beckman scintillation counter.

TABLE 1

Compound A
Experiment A

| Treatment | % of Control | p-value |
|---|---|---|
| 1 $\mu$M Compound A | 93.8 | 0.533 |
| 1 $\mu$M Compound A + 10 $\mu$M Retinol | 94.3 | 0.643 |
| 10 $\mu$M Compound A | 78.1 | 0.0707 |
| 10 $\mu$M Compound A + 10 $\mu$M Retinol | 88.6 | 0.334 |
| 100 $\mu$M Compound A | 12.5 | 0.00052 |
| 100 $\mu$M Compound A + 10 $\mu$M Retinol | 6.2 | 0.00043 |
| 10 $\mu$M Retinol | 98.3 | 0.859 |

TABLE 2

Compound A (n = 3)
Experiment B

| Treatment | % of Control | p-value |
|---|---|---|
| 1 $\mu$M Compound A | 102.1 | 0.770 |
| 1 $\mu$M Compound A + 1 $\mu$M Retinol | 93.3 | 0.147 |
| 1 $\mu$M Compound A + 10 $\mu$M Retinol | 85.4 | 0.024 |
| 10 $\mu$M Compound A | 89.4 | 0.032 |
| 10 $\mu$M Compound A + 1 $\mu$M Retinol | 80.2 | 0.002 |
| 10 $\mu$M Compound A + 10 $\mu$M Retinol | 78.6 | 0.002 |
| 100 $\mu$M Compound A | 23.5 | 0.000011 |
| 100 $\mu$M Compound A + 1 $\mu$M Retinol | 19.7 | 0.000021 |
| 100 $\mu$M Compound A + 10 $\mu$M Retinol | 26.5 | 0.000025 |

TABLE 2-continued

Compound A (n = 3)
Experiment B

| Treatment | % of Control | p-value |
|---|---|---|
| 1 μM Retinol | 103.7 | 0.491 |
| 10 μM Retinol | 100.9 | .801 |
| 28 μM Phenol Red | 86.4 | 0.15 |
| 280 μM Phenol Red | 52.2 | 0.00043 |

TABLE 3

Compound B (n = 4)

| Treatment | % Reduction | p-value |
|---|---|---|
| 1 μM Compound B | 52.1 | 0.0034 |
| 1 μM Compound B + 1 μM Retinol | 24.6 | 0.000129 |
| 1 μM Compound B + 10 μM Retinol | 27.5 | 0.000279 |
| 10 μM Compound B | 65.7 | 0.046248 |
| 10 μM Compound B + 1 μM Retinol | 31.8 | 0.000277 |
| 10 μM Compound B + 10 μM Retinol | 44.1 | 0.001185 |
| 28 μM Phenol Red | 74.7 | 0.075611 |

TABLE 4

Compound D
96 Well Plate (n = 2)

| Treatment | % of Control |
|---|---|
| 10 μM Compound D | 114.3 |
| 10 μM Compound D + 1 μM Retinol | 82.1 |
| 50 μM Compound D | 95.6 |
| 50 μM Compound D + 1 μM Retinol | 25.9 |

TABLE 5

Compound C
96 Well Plate (n = 2)

| Treatment | % of Control |
|---|---|
| 10 μM Compound C | 72.3 |
| 10 μM Compound C + 1 μM Retinol | 45.2 |
| 50 μM Compound C | 34.2 |
| 50 μM Compound C + 1 μM Retinol | 0.3 |

TABLE 6

Compound E
96 Well Plate (n = 2)

| Treatment | % of Control |
|---|---|
| 10 μM Compound E | 148.5 |
| 10 μM Compound E + 1 μM Retinol | 29.1 |
| 50 μM Compound E | 83.9 |
| 50 μM Compound E + 1 μM Retinol | 9.9 |

It can be seen from the results in Tables 1–6, that Compounds A, B and C had sebum suppressive activity. Retinol alone was inactive, but Compounds B through E had improved activity when combined with retinol.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic composition comprising:

(i) from about 0.001% to about 50% of a substituted secondary amine aromatic derivative

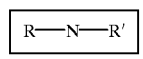

selected from the group consisting of compounds A, B, C, D and E as follows:

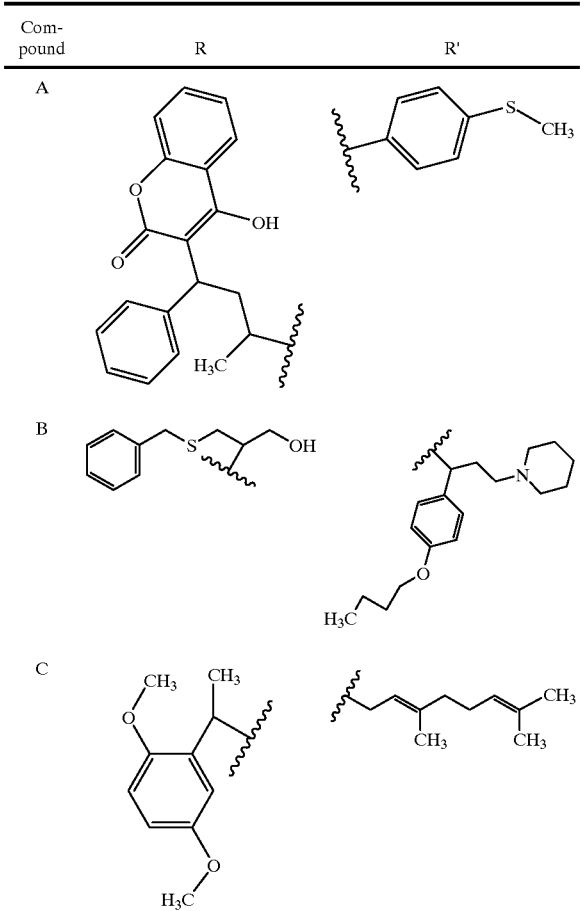

-continued

| Compound | R | R' |
|---|---|---|
| D | 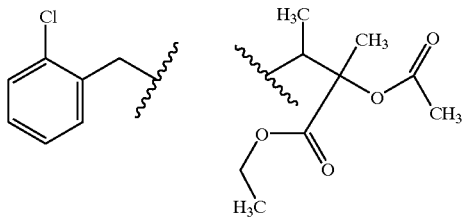 | |

-continued

| Compound | R | R' |
|---|---|---|
| E | 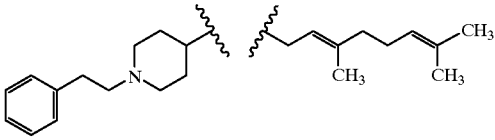 | | and (ii) a cosmetically acceptable vehicle.

2. The composition of claim 1 further comprising a retinoid.

3. A method of reducing oily skin conditions, the method comprising applying to the skin the composition of claim 1.

4. A cosmetic method of reducing sebum secretion from sebocytes, the method comprising applying to the skin the composition of claim 1.

* * * * *